United States Patent [19]

Wolff et al.

[11] Patent Number: 5,145,611
[45] Date of Patent: * Sep. 8, 1992

[54] CARBOXYLIC ACID DERIVATIVES, AND PHARMACEUTICAL COMPOSITIONS CONTAINING THEM

[75] Inventors: Hans P. Wolff, Hirschberg-Grossachsen; Ernst-Christian Witte, Mannheim; Hans-Frieder Kuehnle, Weinheim, all of Fed. Rep. of Germany

[73] Assignee: Boehringer Mannheim GmbH, Mannheim, Fed. Rep. of Germany

[ * ] Notice: The portion of the term of this patent subsequent to Jun. 12, 2007 has been disclaimed.

[21] Appl. No.: 143,456

[22] Filed: Jan. 12, 1988

[30] Foreign Application Priority Data

Jan. 13, 1987 [DE] Fed. Rep. of Germany ....... 3700729

[51] Int. Cl.$^5$ ............... C07C 313/00; C07C 309/00; C07C 317/44; C07C 321/02
[52] U.S. Cl. ............................ 514/532; 554/94; 554/95; 554/101; 554/102; 554/108; 554/109; 554/218; 514/866; 514/574; 514/560; 514/552; 514/550; 514/549; 514/543; 562/429; 562/470; 562/587; 562/588; 564/162; 564/182; 564/191; 564/192; 560/11; 560/15; 560/150; 560/152; 560/155; 560/170
[58] Field of Search ............... 260/399, 400, 402; 514/866, 543, 549, 550, 552, 557, 558, 560, 571; 562/426, 429, 470, 587, 588, 512; 564/162, 182, 191, 192, 204; 560/11, 15, 150, 152, 155, 170

[56] References Cited

U.S. PATENT DOCUMENTS 3,562,330 2/1971 Nordin ........................ 260/5705

FOREIGN PATENT DOCUMENTS 0190682 8/1986 European Pat. Off. .
1382267 1/1975 United Kingdom .
2090591 7/1982 United Kingdom .

OTHER PUBLICATIONS

Doyle et al., Chemical Abstracts, vol. 100:208635b, 1984.

Ager, "The Ester Enolate Claisen Rearrangement of Allyl ... ", Tetrahedron Letters, 23, 3419–20 (1982).
Lythgoe et al., "A New 1,2-Elimination Reaction with a Radical ... ", Tetrahedron Letters, No. 48, 4223–4226 (1977).
Trost et al., "Macrolide Formation via an Isomerization Reaction ... ", J. Am. Chem. Soc., 105, 5940–42 (1983).
Abstract: Prasad et al., "Potential antitubecular drugs, Part I. Synthesis of Derivatives ... ", C.A. 90:49008f (1979).
Trost et al., "Synthesis of Thermodynamically Less Stable Enol Thioethers. An Alternative Oxidative Decarboxylation of α-Thio Acids", J. Org. Chem., 43, 4549–51 (1978).
Trost et al., "Tungsten-Catalyzed Allylic Alkylations. New Avenues for Selectivity", J. Am. Chem. Soc., 105, 7757–9 (1983).

Primary Examiner—Jose G. Dees
Assistant Examiner—Porfirio Nazario
Attorney, Agent, or Firm—Felfe & Lynch

[57] ABSTRACT

Carboxylic acid derivatives of the formula $$R_1-A-\underset{\underset{R_2}{\overset{|}{Y-B}}}{CH}-COOH.$$

$R_1$ is alkoxy, alkylthio, alkylsulphinyl, alkulsulphonyl, alkylamino, cycloalkyl, or cycloalkoxy or optionally substituted aryl, aryloxy, arylthio, arylsulphinyl, arylsulphonyl or arylamino. $R_2$ is optionally substituted aryl or, when B is alkylene also a hydrogen atom. A is a straight-chained or branched, saturated or unsaturated alkylene containing 3 to 10 carbon atoms which is optionally interrupted by a heteratom attached to a saturated carbon and has a chain length of at least 3 atoms. Y is $S(O)_n$ group or oxygen, n being 0, 1 or 2. B is a valency bond or a straight-chained or branched, saturated or unsaturated alkylene containing 1 to 18 carbon atoms. Physiologically acceptable salts, esters and amides thereof are also included. The compounds are useful in the treatment of metabolic diseases.

25 Claims, No Drawings

CARBOXYLIC ACID DERIVATIVES, AND PHARMACEUTICAL COMPOSITIONS CONTAINING THEM

The present invention is concerned with carboxylic acid derivatives, processes for the preparation thereof and pharmaceutical compositions containing them.

The carboxylic acid derivatives useable according to the present invention are compounds of the general formula:

wherein $R_1$ is an alkoxy, alkylthio, alkylsulphinyl, alkylsulphonyl, alkylamino, cycloalkyl or cycloalkoxy radical or an optionally substituted aryl, aryloxy, arylthio, arylsulphinyl, arylsulphonyl or arylamino radical, $R_2$ is an optionally substituted aryl radical or, when B is an alkylene radical is also a hydrogen atom, A is a straight-chained or branched, saturated or unsaturated alkylene radical containing 3 to 10 carbon atoms which is optionally interrupted by a heteroatom and has a chain length of at least 3 atoms, with the proviso that a heteroatom is not attached to an unsaturated aliphatic carbon atoms, Y is an $S(O)_n$ group or an oxygen atom, n is 0, 1 or 2 and B is a valency bond or a straight-chained or branched, saturated or unsaturated alkylene radical containing up to 18 carbon atoms, as well as the physiologically acceptable salts, esters and amides thereof.

Of the compounds of general formula I, only a few examples are known and the pharmacological action according to the present invention has hitherto not been described.

2-Phenoxy-5-phenylpentanoic acid was described by Nordin in U.S. Pat. No. 3,562,300 as a precursor of anti-arrhythmically active amines. Methyl 5-phenyl-2-phenylsulphonyl-4-pentenoate was described by Trost and Hung, J.A.C.S., 105, 7757 (1983), as an intermediate. Thus, all of the compounds of general Formula I are new compounds with the additional proviso that, when $R_1$ is phenyl and A is a straight-chained saturated or ethylenically unsaturated alkylene radical, the minimum chain length is 4 atoms.

Similarly structured compounds not included in general formula I are 2-methyl-2-methylthio-5-phenylpentanoic acid and phenyl-substituted analogues, as well as 2-methyl-2-methylthio-6-(3-methoxyphenyl)-hexanoic acid and 2-methyl-2-methylthio-7-(3,4-methylenedioxyphenyl)-heptanoic acid which were used by Trost et al., J. Org. Chem. 43, 4559 (1978), as intermediates for the preparation of enol thioethers.

The compounds of general formula I possess valuable pharmacological properties. They can be used for the treatment of diabetes and prediabetes and especially for the treatment of maturity onset diabetes.

Structurally and in the nature of their action, the compounds of general formula I bear no relationship to the known antidiabetes. They lower the blood sugar level by increasing the peripheral glucose oxidation, their action depending upon an increase of the sensitivity of peripheral tissues towards insulin. In contra-distinction to the biguanides, no increase of the blood lactate values is thereby observed. Therefore, the compounds of general formula I also represent a valuable enrichment for treatment of non-diabetic disease states in which an insulin resistance is present, for example adipositas and atherosclerosis.

In addition, they show a marked lipid-sinking action and can, therefore, also be used for the treatment of fat metabolism diseases.

The alkyl radicals of the substituent $R_1$ are to be understood to be saturated or unsaturated, straight-chained or branched aliphatic hydrocarbon radicals containing up to 8 carbon atoms, the methyl, t-butyl, n-hexyl and n-octyl radicals being especially preferred.

The cycloalkyl and cycloalkoxy radicals are to be understood to be saturated carbocyclic rings with 3 to 10 carbon atoms which possibly form bi- and tricyclic systems and carry substituents, such as halogen atoms or lower alkyl radicals. The cyclopentyl, cyclohexyl, 1-methylcyclohexyl, cyclohexyloxy and 1-methylcyclohexyloxy radicals are especially preferred.

The aryl radicals are to be understood to be aromatic hydrocarbon radicals with 6 to 14 carbon atoms, the phenyl and naphthyl radicals being preferred.

Substituted aryl radicals are, in all definitions, to be understood to be those aromatic hydrocarbon radicals with 6 to 14 carbon atoms which, in one or more positions, carry hydroxyl groups, halogen atoms, lower alkyl, lower alkoxy or trifluoromethyl radicals, cyano or nitro groups or amino groups optionally substituted once or twice by lower alkyl radicals. Phenyl and naphthyl radicals substituted by the above-mentioned groups are preferred. Especially preferred are the phenyl, 4-methylphenyl, 4-t-butylphenyl, 4-methoxyphenyl, 3-trifluoromethylphenyl and 4-chlorophenyl radicals. Halogen is to be understood to be a fluorine, chlorine, bromine or iodine atom and preferably a fluorine, chlorine or bromine.

Lower alkyl and alkoxy radicals can contain up to 6 carbon atoms, the methyl, ethyl, methoxy and ethoxy radicals being preferred.

Unbranched alkylene radicals A are preferably the following:
a) $-(CH_2)_m-$ with $m=3$ to $10$ and $-(CH_2)_p-X-(CH_2)_q-$ with $p=2-8$ and $q=1-6$, m, p and q being whole numbers and the sum of p and q is not greater than 10 and X is an oxygen or sulphur atom or an NH group.
b) When $R_1$ is an aryl radical, A can also be one of the following: $-CH_2-X-(CH_2)_q-$, $-CH=CHCH_2-$, $-C\equiv CCH_2-$, $-C\equiv C(CH_2)_p-$, $-CH=CHCH_2-X-(CH_2)_q-$, $-C\equiv CCH_2-X-(CH_2)_q-$, wherein p, q and X have the above-given meanings.

The branched alkylene groups can be, for example:
a)

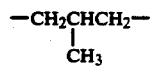

and
b) when $R_1$ is an aryl radical, also the following:

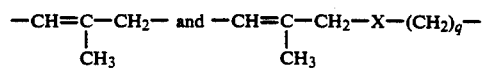

wherein X and q have the above-given meanings.

An alkylene radical B is especially a —(CH$_2$)$_r$—, —CH$_2$—CH=CH—, —CH$_2$C≡C— or —CH=CH— radical, wherein r is a whole number of from 1 to 18.

The physiologically acceptable salts are preferably alkali metal, alkaline earth metal and ammonium salts, as well as salts with blood sugar-lowering biguanides.

The esters derived from the carboxylic acids of general formula I contain, as alcohol components, lower monohydroxy alcohols, of which methanol, ethanol and n-butanol are preferred, as well as polyhydroxy alcohols, for example glycerol, or alcohols with other functional groups, for example ethanolamine.

The amides according to the present invention derived from carboxylic acids of general formula I contain, as amine component, preferably ammonia, p-aminobenzoic acid, β-alanine, ethanolamine or 2-aminopropanol. However, alkylamines, for example isopropylamine or tert.-butylamine, dialkylamines, for example diethylamine, as well as cyclic amines, for example morpholine and 4-substituted piperazines, can also be used.

The substituted carboxylic acids of general formula I have a centre of chirality. Therefore, the above-given definition of the compounds according to the present invention also includes all possible enantiomers, mixtures thereof and the racemates.

Preferred carboxylic acid derivatives of general formula I are compounds in which R$_1$ is an alkoxy, alkylthio, alkylsulphinyl, alkylsulphonyl, alkylamino, cycloalkyl, cycloalkoxy, phenyl, phenoxy, phenylthio, phenylsulphinyl, phenylsulphonyl or phenylamino radical, wherein the phenyl radicals can be substituted one or more times by hydroxyl, halogen, C$_1$-C$_6$-alkyl, C$_1$-C$_6$-alkoxy, trifluoromethyl, cyano, nitro, amino, alkylamino or dialkylamino, R$_2$ is a phenyl radical which is optionally substituted one or more times by the substituents mentioned in the case of R$_1$ and, when B is an alkylene radical, can also be a hydrogen atom, A is a straight-chained or branched, saturated or unsaturated alkylene radical containing 3 to 10 carbon atoms which is optionally interrupted by a heteroatom and has a chain length of at least 3 atoms, with the proviso that a heteratoma is not to be attached to an unsaturated aliphatic carbon atom, Y is an S(O)$_n$ group or an oxygen atom, n is 0, 1 or 2 and B is a valency bond or a straight-chained or branched, saturated or unsaturated alkylene radical containing up to 5 carbon atoms, as well as the physiologically acceptable salts, esters and amides thereof.

Especially preferred are carboxylic acid derivatives of general formula I in which R$_1$ is a phenyl or phenoxy radical which can optionally be substituted one or more times by halogen, C$_1$-C$_6$-alkyl, C$_1$-C$_6$-alkoxy and trifluoromethyl, R$_2$ is a phenyl radical which can optionally be substituted one or more times by the substituents mentioned in the case of R$_1$ and, when B is an alkylene radical, can also be a hydrogen atom, A is a straight-chained or branched, saturated or unsaturated alkylene radical containing 3 to 10 carbon atoms which is interrupted by a heteroatom and has a chain length of at least 3 atoms, with the proviso that a heteroatom is not attached to an unsaturated aliphatic carbon atoms, Y is an S(O)$_n$ group or an oxygen atom, n is 0, 1 or 2 and B is a valency bond or a straight-chained or branched, saturated or unsaturated alkylene radical containing up to 5 carbon atoms, as well as the physiologically acceptable salts, esters and amides thereof.

Another group of preferred compounds are the novel compounds of general Formula I in which: R$_1$ is C$_1$-C$_8$ alkoxy, C$_1$-C$_8$ alkylthio, C$_1$-C$_8$ alkylamino, C$_5$ or C$_6$ cycloalkyl, C$_5$ or C$_6$ cycloalkoxy optionally substituted by methyl or is optionally substituted phenyl, phenyloxy, phenylthio, phenylsulpinyl, phenylsulphonyl, or phenylamino, the substituents being halogen, C$_1$-C$_4$ alkyl or trifuloromethyl; R$_2$ is phenyl optionally substituted by halogen, C$_1$-C$_4$ alkyl, methoxy, trifluoromethyl, methylamino or dimethylamino, or, when B is an alkylene radical, also a hydrogen atom; A is C$_4$-C$_8$ alkylene with at least 4 carbon atoms in a straight chain, C$_4$-C$_6$ alkenylene or C$_3$-C$_6$ alkynylene with at least 3 carbon atoms in a straight chain, alkylene-X-alkylene in which each alkylene has from 1 to 4 carbon atoms and X is oxygen, sulphur or —NH—, alkenylene-O-alkylene in which the alkenylene has from 3 to 5 carbon atoms and the oxygen atom is not attached to an unsaturated carbon atom and the alkylene has from 1 to 3 carbon atoms, or alkynylene-O-alkylene in which the alkynylene has 3 or 4 carbon atoms and the oxygen atom is not attached to an unsaturated carbon atom and the alkylene has from 1 to 3 carbon atoms; Y is an S(O)$_n$ group or an oxygen atom in which n is 0, 1, or 2; and B is a valency bond or C$_1$-C$_8$ alkyl or C$_2$-C$_8$ alkenyl.

Particularly preferred new compounds are those compounds of Formula I in which:

R$_1$ is methoxy; methylthio; methylamino; cyclopentyl; cyclohexyl; cyclohexyloxy; 1-methylcyclohexyloxy; phenyl optionally substituted by methyl, tert.-butyl, chlorine or trifluoromethyl; phenoxy optionally substituted by fluorine, chlorine, methyl or trifluoromethyl; phenylthio optionally substituted by chlorine; phenylsulphinyl optionally substituted by chlorine; phenylsulphonyl optionally substituted by chlorine; or phenylamino optionally substituted by chlorine;

R$_2$ is phenyl optionally substituted by chlorine, C$_1$-C$_4$ alkyl, methoxy, trifluoromethyl or dimethylamino, or, when B is alkylene, also a hydrogen atom;

A is —(CH$_2$)$_{m'}$— with m'=4 to 10; —(CH$_2$)$_{q'}$—O—(CH$_2$)$_{q'}$— with q'=1 to 3; —C≡CCH$_2$—; —C≡C(CH$_2$)$_3$—; —(CH$_2$)$_2$—S—(CH$_2$)$_2$—; —(CH$_2$)$_2$—NH—(CH$_2$)$_2$—;

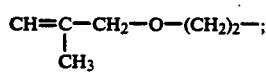

or C≡C—CH$_2$—O—(CH$_2$)$_2$—;

Y is oxygen, sulphur or —SO$_2$—; and

B is a valency bond, C$_1$-C$_8$ alkylene (particularly methylene, ethylene, tert.-butylene, n-hexylene or n-octylene), or —CH$_2$—CH=CH—.

The present invention also provides processes for the preparation of the compounds of general formula I, wherein A. a compound of the general formula:

$$Z-\underset{X}{CH}-W \quad (II)$$

in which W is —COOR$_3$ or another group convertible into the carboxyl function, X is a reactive residue and Z is a hydrogen atom or an R$_1$—A— radical, in which R$_1$ and A have the above-given meanings, and R$_3$ is a lower alkyl radical, is reacted with a compound of the general formula:

$$R_2-B-YH \quad (III),$$

in which R$_2$, B and Y have the above-given meanings, to give a compound of the general formula:

$$Z-\underset{Y-B-R_2}{CH}-W \quad (IV)$$

and optionally subsequently thereto
a) the group W is converted into the free carboxyl function or into a physiologically acceptable ester or amide,
b) when Y is a sulphur atom, it is converted into an SO or SO$_2$ group, or
c) when Z is a hydrogen atom, either
C1) alkylation is carried out with a compound of the general formula:

$$R_1-A-X \quad (V)$$

in which R$_1$ and A have the above-given meanings and X is a reactive group, or
C2) condensation is carried out with a compound of the general formula:

$$R_1-A'-CHO \quad (V'),$$

in which A' is an alkylene radical A shortened by a —CH$_2$— group and R$_1$ has the above-given meaning, and, subsequent to the condensation, the resultant double bond is hydrogenated and a compound IV obtained by the above-mentioned process step C1) or C2) in which Z is R$_1$A— is converted in the above-mentioned manner on the groups W or Y or B. a compound of the general formula:

$$R_1-A-\underset{YH}{CH}-W, \quad (VI)$$

in which R$_1$, A, Y and W have the above-given meanings, is reacted with a compound of the general formula:
$$R_2-B-X \quad (VII),$$

in which R$_2$, B and X have the above-given meanings, to give a compound of general formula IV which is optionally converted in the above-described way on the groups W and Y.

The preparation of the starting compounds can take place in known manner by alkylating, for example, malonic esters with compounds of general formula V and reacting the derivatives obtained of the general formula:

$$R_1-A-\underset{R_4}{\overset{COOR_3}{\underset{|}{C}}}\diagdown_{COOR_3}, \quad (VIII)$$

in which R$_1$, A and R$_3$ have the above-given meanings and R$_4$ is a hydrogen atom, to give compounds VIII, in which R$_4$ is a reactive group X, subsequently converting these by decarboxylation into the compounds of general formula II, in which W is a —COOR$_3$ group and Z is an R$_1$—A— group, and optionally then converting these into compounds of general formula VI.

The reaction of the reactive carboxylic acid derivatives of general formula II with the compounds of general formula III preferably takes place with the addition of an acid-binding agent, for example sodium hydrogen carbonate, potassium carbonate, sodium ethylate or sodium hydride, esters of the reactive carboxylic acid derivatives preferably being used for the reaction. As inert solvents, there can be used, for example, diethyl ether, benzene, tetrahydrofuran, dioxan or methylene chloride. When using inorganic bases, as reaction medium there can also be used, for example, ethanol, butan-2-one, dimethylformamide, hexamethylphosphoric acid triamide or acetonitrile. The reactive residues X can be, for example, halides or sulphonic acid ester groups, especially chloride, bromide, p-toluenesulphonyloxy or methanesulphonyloxy.

The reaction of compounds IV, in which Z is a hydrogen atom, with aldehydes of general formula VI according to process C2) takes place under conditions such as are usual for the condensation of activated methylene groups with keto compounds. The condensation is preferably carried out in pyridine or dimethylformamide with the addition of a catalytic amount of a strong base, for example piperidine. To the reaction mixture, it is advantageous to add an appropriate solvent, for example benzene, in order to be able to distil off azeotropically the water of reaction.

The subsequent hydrogenation of the resultant double bond is carried out in the usual way with catalytically activated hydrogen at normal pressure or at an elevated pressure. A catalysts, there can be used metal catalysts, for example Raney nickel or palladium-charcoal. As solvents, there can be used, for example, acetic acid or lower alcohols and, in the case of carboxylic acids IV, also aqueous alkalis.

The reaction of the reactive derivatives V with compounds of general formula IV, in which Z is a hydrogen atom, and of the reactive derivatives VII with compounds of the general formula VI preferably takes place with the addition of a strong base, for example sodium ethylate, sodium hydride or 1,8-diazabicyclo-(5,4,0)-undec-7-ene. As inert solvents, there can be used, for example, ethanol, dimethyl sulphoxide, toluene or benzene. Furthermore, there can be used, for example, dimethylformamide or hexamethylphosphoric acid triamide as solvents. The reaction is preferably carried out at ambient temperature or at a moderately elevated temperature or at the boiling temperature of the solvent used. The reactive residues X can be, for example, halides or sulphonic acid ester groups, especially chloride, bromide, p-toluenesulphonyloxy or methanesulphonyloxy.

The oxidation of compounds of general formula IV, in which Y is a sulphur atom, to sulphoxides or sulphones is preferably carried out with hydrogen peroxide in a polar solvent, such as glacial acetic acid, a mixture of glacial acetic acid and acetic anhydride or acetone. Oxidation with trifluoroperacetic acid has proved to be especially advantageous, in which case, as solvent, it is preferable to use trifluoroacetic acid.

The group W convertible into a carboxyl function is especially to be understood to be a nitrile group or a residue which can be converted oxidatively into a carboxyl group. The oxidisable groups are preferably the hydroxymethyl, aminomethyl and formyl radicals or functional derivatives of these radicals. The oxidation can be carried out with conventional oxidation agents, for example manganese IV compounds, permanganates or dichromates or, in the case of the formyl radical, also with atmospheric oxygen and silver oxide.

The conversion of the substituent W possibly to be carried out subsequent to the condensation to the compounds of the general formula IV takes place, for example, by saponification of a carboxylic acid ester to the corresponding carboxylic acid with a mineral acid or alkali metal hydroxide in a polar solvent, for example water, methanol, ethanol, dioxan or acetone. The saponification is advantageously carried out with a strong base, for example sodium or potassium hydroxide, in a mixture of methanol and water at ambient temperature or at a moderately elevated temperature. On the other hand, however, a carboxylic acid can also be esterified in the usual way or an ester with a particular residue $R_4$ can be converted by transesterification into an ester with a different residue $R_4$. The esterification of the carboxylic acids is preferably carried out in the presence of an acidic catalyst, for example hydrogen chloride, sulphuric acid, p-toluenesulphonic acid or a strongly acidic ion exchange resin.

Transesterifications, on the other hand, require the addition of a small amount of a basic substance, for example of an alkali metal or alkaline earth metal hydroxide or of an alkali metal alcoholate. For the esterification of the carboxyl group or for the transesterification, there can, in principle, be used all alcohols. Preferred are the lower monohydroxy alcohols, for example methanol, ethanol or propanol, as well as polyhydroxy alcohols, for example glycerol, or alcohols with other functional groups, for example ethanolamine.

The amides according to the present invention derived from the carboxylic acids of general formula I are preferably prepared according to known methods from the carboxylic acids or the reactive derivatives thereof, for example carboxylic acid halides, esters, azides, anhydrides or mixed anhydrides, by reaction with amines. As amine components, there can be used, for example, ammonia, alkylamines and dialkylamines, but also aminoalcohols, for example ethanolamine and 2aminopropanol, as well as amino acids, for example p-aminobenzoic acid, β-alanine and the like. Other valuable amino components include the alkyl-, aralkyl- and arylpiperazines.

However, the above amides can also be prepared by partial saponification of the nitriles derived from the carboxylic acids according to the present invention. The saponification takes place in dilute mineral acids at moderately elevated temperatures, in alkaline hydroperoxide solution or advantageously in 98% sulphuric acid or polyphosphoric acid.

For the preparation of salts with pharmacologically acceptable organic or inorganic bases, for example sodium hydroxide, potassium hydroxide, calcium hydroxide, ammonium hydroxide, methylglucamine, morpholine or ethanolamine, the carboxylic acids can be reacted with the corresponding bases. Mixtures of the carboxylic acids with an appropriate alkali metal carbonate or hydrogen carbonate can also be used.

For the preparation of pharmaceutical compositions, compounds of general formula I are mixed in known manner with appropriate pharmaceutical carrier substances, aroma, flavouring and colouring materials and formed, for example, into tablets or dragees or, with the addition of appropriate adjuvants, suspended or dissolved in water or an oil, for example olive oil.

The compounds of general formula I can be administered orally and parenterally in liquid or solid form. As injection medium, water is preferably used which contains the stabilising agents, solubilising agents and/or buffers usual in the case of injection solutions. Examples of such additives include tartrate and borate buffers, ethanol, dimethyl sulphoxide, complex formers (such as ethylenediamine-tetraacetic acid), high molecular weight polymers (such as liquid polyethylene oxide) for viscosity regulation and polyethylene derivatives of sorbit anhydrides.

Examples of solid carrier materials include starch, lactose, mannitol, methyl cellulose, talc, highly dispersed silicic acid, high molecular weight fatty acids (such as stearic acid), gelatine, agar-agar, calcium phosphate, magnesium stearate, animal and vegetable fats and solid high molecular weight polymers (such as polyethylene glycols). Composition suitable for oral administration can, if desired, contain flavouring and sweetening agents.

The dosage administered depends upon the age, the state of health and the weight of the recipient, the extent of the disease, the nature of further treatments possibly carried out simultaneously, the frequency of the treatment and the nature of the desired action. Usually, the daily dose of the active compound is from 0.1 to 50 mg./kg. of body weight. Normally, 0.5 to 40 and preferably 1.0 to 20 mg./kg./day in one or more administration per day are effective in order to achieve the desired results.

Preferred according to the present invention are, apart from the compounds of general formula I mentioned in the Examples, as well as the amides, methyl- and ethylesters thereof, also the following compounds:

8-methoxy-2-(4-methylphenoxy)-octanoic acid
8-methoxy-2-(4-methylphenylthio)-octanoic acid
8-methoxy-2-(2-phenylethylsulphonyl)-octanoic acid
8-methylthio-2-(4-methylphenoxy)-octanoic acid
8methylthio-2-(4-methylphenylthio)-octanoic acid
8-methylamino-2-(4-methylphenylsulphonyl)-octanoic acid
6-cyclopentyl-2-(4-methylphenylsulphonyl)-hexanoic acid
6-cyclohexyl-2-(4-methylphenylsulphonyl)-hexanoic acid
6-cyclohexyloxy-2-(4-methylphenylsulphonyl)-hexanoic acid
6(1-methylcyclohexyloxy)-2-(4-methylphenylsulphonyl)-hexanoic acid
8-cyclohexyl-2-(4-methylphenylsulphonyl)-octanoic acid 5-(4-methylphenyl)-2-(4-methylphenylsulphonyl)-4-pentynoic acid; m.p. 134°–135° C.; ethyl ester m.p. 65° C.
5-(4-t-butylphenyl)-2-(4-methylphenylsulphonyl)-4-pentynoic acid, colourless oil
5-(4-chlorophenyl)-2-t-butoxy-4-pentynoic acid
5(4-chlorophenyl)-2-phenoxy-4-pentynoic acid
5-(4-chlorophenyl)-2-(4-methylphenoxy)-4-pentynoic acid
5-(4-chlorophenyl)-2-(4-t-butylphenoxy)-4-pentynoic acid
5-(4-chlorophenyl)-2-(4-chlorophenoxy)-4-pentynoic acid
5-(4-chlorophenyl)-2-(4-methoxyphenoxy)-4-pentynoic acid
5-(4-chlorophenyl)-2-(2-phenylethoxy)-4-pentynoic acid
5-(4-chlorophenyl)-2-(phenylthio)-4-pentynoic acid
5-(4-chlorophenyl)-2-(4-methylthio)-4-pentynoic acid; m.p. 110°–112° C.
5-(4-chlorophenyl)-2-(4-t-butylphenylthio)-4-pentynoic acid
5-(4-chlorophenyl)-2-(4-chlorophenylthio)-4-pentynoic acid
5-(4-chlorophenyl)-2-(4-methoxyphenylthio)-4-pentynoic acid
5-(4-chlorophenyl)-2-(2-phenylethylthio)-4-pentynoic acid
5-(4-chlorophenyl)-2-(4-t-butylphenylsulphonyl)-4-pentynoic acid
5-(4-chlorophenyl)-2-(2-phenylethenylsulphonyl)-4-pentynoic acid
5-(4-chlorophenyl)-2-(2-phenylethylsulphonyl)-4-pentynoic acid
5-(4-chlorophenyl)-2-(4-chlorocinnamylsulphonyl)-4-pentynoic acid
7-(4-(chlorophenyl)2-(4-methylphenylsulphonyl)-6-heptynoic acid
5-(4-methoxyphenyl)-2-(4-methylphenoxy)-4-pentynoic acid
5-(4-methoxyphenyl)-2-(4-methylphenylthio)-4-pentynoic acid
7-phenyl-2-(2-phenylethoxy)-heptanoic acid
7-phenyl-2-(2-phenylethylthio)-heptanoic acid
7-phenyl-2-(benzylsulphonyl)-heptanoic acid; oil
7-phenyl-2-[2-(4-methylphenyl)-ethylsulphonyl]-heptanoic acid
7-2-[2-(4-t-butylphenyl)-ethylsulphonyl]-heptanoic acid
7-phenyl-2-[2-(4-chlorophenyl)-ethylsulphonyl]-heptanoic acid
7-phenyl-2-[2-(4-methoxyphenyl)-ethylsulphonyl]-heptanoic acid
7-phenyl-2-(2-phenylethenylsulphonyl)-heptanoic acid
7-phenyl-2-(3-phenylpropylsulphonyl)-heptanoic acid; oil
7phenyl-2-(4-chlorocinnamoylsulphonyl)-heptanoic acid
8-phenyl-2-(4-t-butylphenoxy)-octanoic acid; m.p. 51°–53° C.
8-phenyl-2-(4-t-butylphenylthio)-octanoic acid
8-phenyl-2-(4-ethylphenylsulphonyl)-octanoic acid; m.p. 72°–73° c.
8-phenyl-2-(4-propylphenylsulphonyl)-octanoic acid; m.p. 75°–76° C.
8-phenyl-2-(4-t-butylphenylsulphonyl)-octanoic acid
8-phenyl-2-(2-phenylethylsulphonyl)-octanoic acid; m.p. 131°–133° C.
7-(4-chlorophenyl)-2-(4-t-butylphenoxy)-heptanoic acid; oil
7-(4-chlorophenyl)-2-(2-phenylethoxy)-heptanoic acid
7-(4-chlorophenyl)-2-(2-methylphenylthio)-heptanoic acid; m.p. 55°–56° C.
7-(4-chlorophenyl)-2-(4-t-butylphenylthio)-heptanoic acid
7-(4-chlorophenyl)-2-(2-phenylethylthio)-heptanoic acid; m.p. 58°–60° C.
7-(4-chlorophenyl)-2-(ethylsulphonyl)-heptanoic acid
7-(4-chlorophenyl)-2-(butylsulphonyl)-heptanoic acid
7-(4-chlorophenyl)-2-(t-butylsulphonyl)-heptanoic acid
7-(4-chlorophenyl)-2-(octylsulphonyl)-heptanoic acid
7-(4-chlorophenyl)-2-(4-t-butylphenylsulphonyl)-heptanoic acid
7-(4-chlorophenyl)-2-(2-phenylethylsulphonyl)-heptanoic acid; m.p. 54°–56° C.
7-(4-chlorophenyl)-2-(6-phenylhexylsulphonyl)-heptanoic acid
8-(4-chlorophenyl)-2-(4-t-butylphenoxy)-octanoic acid
8-(4-chlorophenyl)-2-(2-phenylethoxy)-octanoic acid
8-(4-chlorophenyl)-2-(4-t-butylphenylthio)-octanoic acid
8-(4-chlorophenyl)-2-(2-phenylethylthio)-octanoic acid
8-(4-chlorophenyl)-2-(2-methylphenylsulphonyl)-octanoic acid; m.p. 82°–85° .; ethyl ester: oil
8-(4-chlorophenyl)-2-(4-ethylphenylsulphonyl)-octanoic acid
8-(4-chlorophenyl)-2-(4-propylphenylsulphonyl)-octanoic acid
8-(4-chlorophenyl)-2-(4-t-butylphenylsulphonyl)-octanoic acid
8-(4-chlorophenyl)-2-(2-phenylethylsulponyl)-octanoic acid
8-(4-chlorophenyl)-2-[2-(4-methylphenyl)-ethylsulphonyl]-octanoic acid
8-(4-chlorophenyl)-2-[2-(4-chlorophenyl)-ethylsulphonyl]-octanoic acid
8-(4-chlorophenyl)-2-[2-(4-methoxyphenyl)-ethyl-sulphonyl]-octanoic acid
7-(4-methoxyphenyl)-2-(4-t-butylphenoxy)-heptanoic acid
7-(4-methoxyphenyl)-2-(4-t-butylphenylthio)-heptanoic acid
7-(4-methoxyphenyl)-2-(4-t-butylphenylsulphonyl)-I
7-(4-methoxyphenyl)-2-(2-phenylethylsulphonyl)-heptanoic acid
7-(4-methoxyphenyl)-2-[2-(4-methylphenyl)-ethyl-sulphonyl]-heptanoic acid
7-(4-methoxyphenyl)-2-[2-(4-chlorophenyl)-ethyl-sulphonyl]-heptanoic acid
3-(2-phenylethoxy)-2-(4-methylphenoxy)-propionic acid
3-(2-phenylethoxy)-2-(4-methylphenylsulphonyl)-propionic acid
3-(3-phenylpropoxy)-2-(4-methylphenoxy)-propionic acid
3-(3-phenylpropoxy)-2-(4-methylphenylthio)-propionic acid
3-(3-phenylpropoxy)-2-(4-methylphenylsulphonyl)-propionic acid
4-(2-phenylethoxy)-2-(4-methylphenoxy)-butyric acid
4-(2-phenylethoxy)-2-(4-methylphenylthio)-butyric acid
4-(2-phenylethoxy)-2-(4-methylphenylsulphonyl)-butyric acid
4-(2-phenylethoxy)-2-(2-phenylethylsulphonyl)-butyric acid 5-benzyloxy-2-(4-methylphenoxy)-pentanoic acid
5-benzyloxy-2-(4-methylphenylsulphonyl)-pentanoic acid
4-cinnamyloxy-2-(4-methylphenoxy)-butyric acid
4-cynnamyloxy-2-(4-methylphenylthio)-butyric acid
4-cinnamyloxy-2-(4-methylphenylsulphonyl)-butyric acid
4(2-methyl-3-phenyl-2-propenyloxy)-2-(4-methylphenoxy)-butyric acid
4(2-methyl-3-phenyl-2-propenyloxy)-2-(4-methylphenylthio)-butyric acid
4(2-methyl-3-phenyl-2-propenyloxy)-2-(4-methylphenylsulphonyl)-butyric acid
4-[2-(4-chlorophenyl)-ethoxy]-2-methoxybutyric acid
4-[2-(4-chlorophenyl)-ethoxy]-2-hexyloxybutyric acid
4-[2-(4-chlorophenyl)-ethoxy]-2-(methylthio)-butyric acid
4-[2-(4-chlorophenyl)-ethoxy]-2-(hexylthio)-butyric acid
4-[2-(4-chlorophenyl)-ethoxy]-2-methylsulphonylbutyric acid
4-[2-(4-chlorophenyl)-ethoxy]-2-hexylsulphonylbutyric acid
3-[2-(4-chlorophenyl)-ethoxy]-2-(4-methylphenoxy)-propionic acid
3-[2-(4-chlorophenyl)-ethoxy]-2-(4-methylphenylsulphonyl)-propionic acid
3-[3-(4-chlorophenyl)-propoxy]-2-(4-methylphenoxy)-propionic acid
3-[3-(4-chlorophenyl)-propoxy]-2-(4-methylphenylthio)propionic acid
3-[3-(4-chlorophenyl)-propoxy]-2-(4-methylphenylsulphonyl)-propionic acid
4-[2-(4-chlorophenyl)-ethoxy]-2-(4-methylphenoxy)-butyric acid; m.p. 75°-76° C.
4-[2-(4-chlorophenyl)-ethoxy]-2-(4-methylphenylthio)-butyric acid
4-[2-(4-chlorophenyl)-ethoxy]-2-(2-phenylethylsulphonyl)-butyric acid
4-[2-(4-chlorophenyl)-ethoxy]-2-[2-(4-methylphenyl)-ethylsulphonyl]-butyric acid
4-[2-(4-chlorophenyl)-ethoxy]-2-(3-trifluoromethylphenylsulphonyl)-butyric acid
4-[2-(4-chlorophenyl)-ethoxy]-2-(4-methoxyphenylsulphonyl)butyric acid
4-[2-(4-chlorophenyl)-ethoxy]-2-(4-dimethylaminophenylsulphonyl)-butyric acid
4-(3-trifluoromethylphenyl)-2-(4-methylphenylsulphonyl)butyric acid
5-(4-chlorobenzyloxy)-2-(4-methylphenoxy)-pentanoic acid
5-(4-chlorobenzyloxy)-2-(4-methylphenylthio)-pentanoic acid
5-(4-chlorobenzyloxy)-2-(4-methylphenylsulphonyl)-pentanoic acid
5-(4-chlorobenzyloxy)-2-(2-phenylethylsulphonyl)-pentanoic acid
4-(4-chlorocinnamyloxy)-2-(4-methylphenoxy)-butyric acid
4-[3-(4-chlorophenyl)-2-propynyloxy]-2-(4-methylphenoxy)-butyric acid
4-(4-chlorocinnamyloxy)-2-(4-methylphenylthio)-butyric acid
4-[3-(4-chloropenyl)-2-propynyloxy]-2-(4-methylphenylthio)-butyric acid
4(4-chlorocinnamyloxy)-2-(4-methylphenylsulphonyl)-butyric acid 4-[3-(4-chlorophenyl)-2-propynyloxy]-2-(4-methylphenylsulphonyl)-butyric acid 6-phenoxy-2-(4-methylphenoxy)-hexanoic acid
6-phenoxy-2-(4-t-butylphenoxy)-hexanoic acid
6-phenoxy-2-(4-methylphenylthio)-heptanoic acid
6-phenoxy-2-(4-methylphenylsulphonyl)-heptanoic acid
7-phenoxy-2-(4-methylphenoxy)-heptanoic acid
7-phenoxy-2-(4-methylphenylthio)-heptanoic acid
7-phenoxy-2-(4-methylphenylsulphonyl)-heptanoic acid
6-phenoxy-2-(2-phenylethylsulphonyl)-heptanoic acid
6-phenoxy-2-(4-methylphenylthio)-heptanoic acid
6-phenoxy-2-(4-methylphenoxy)-heptanoic acid
6-phenoxy-2-(4-methylphenylsulphonyl)-heptanoic acid
6-phenoxy-2-(4-methylphenoxy)-heptanoic acid
6-phenoxy-2-(4-methylphenylsulphonyl)-heptanoic acid
6-phenoxy-2-(4-methylphenylsulphonyl)-heptanoic acid
6(4-chlorophenoxy)-2-(4-methylphenoxy)-hexanoic acid; m.p. 93°-95° C.
7(4-chlorophenoxy)-2-(4-methylphenoxy)-heptanoic acid; m.p. 102°-104° C.
6-4-chlorophenyl)-2-(4-t-butylphenoxy)-heptanoic acid; m.p. 108°-109° C.
6-4-chlorophenoxy)-2-(4-chlorophenoxy)-heptanoic acid
6-4-chlorophenoxy)-2-(4-methylphenylthio)-heptanoic acid; m.p. 92°-93° C.
6-4-chlorophenoxy)-2-(2-phenylethylsulphonyl)-heptanoic acid
6-4-chlorophenothio)-2-(4-methylphenoxy)-heptanoic acid
6-4-chlorophenthio)-2-(4-methylphenylsulphonyl)-heptanoic acid
6-4-chlorophenthio)-2-(4-methylphenoxy)-heptanoic acid
6-4-chlorophensulphinyl)-2-(4-methylphenoxy)-heptanoic acid
6-4-chlorophensulphonyl)-2-(4-methylphenoxy)-heptanoic acid
7-(4-fluorophenoamino)-2-(4-methylphenoxy)-heptanoic acid
7-(4-fluorophenoxy)-2-(4-methylphenylthio)-heptanoic acid
7-(4-fluorophenoxy)-2-(4-methylphenylsulphonyl)-heptanoic acid
7-(4-methylphenoxy)-2-(4-methylphenoxy)-heptanoic acid
7-(4-methylphenoxy)-2-(4-methylphenylthio)-heptanoic acid
7-(4-methylphenoxy)-2-(4-methylphenylsulphonyl)-heptanoic acid
7-(4-methylphenoxy)-2-(4-methylphenoxy)-heptanoic acid
7-(4-methylphenoxy)-2-(4-methylphenylthio)-heptanoic acid
7-(4-methylphenoxy)-2-(4-methylphenylsulphonyl)-heptanoic acid
7-(3-trifluoromethylphenoxy)-2-(4-methylphenoxy)-heptanoic acid
7-(3-trifluoromethylphenoxy)-2-(4-methylphenylsulphonyl)-heptanoic acid
4-(2-phenoxyethoxy)-2-(4-methylphenoxy)-butyric acid
4-(2-phenoxyethoxy)-2-(4-methylphenylthio)-butyric acid
4-(2-phenoxyethoxy)-2-(4-methylphenylsulphonyl)-butyric acid 4-[2-(4-methylphenoxy)-ethoxy]-2-(4-methylphenoxy)-butyric acid 4-[2-(4-methylphenoxy)-ethoxy]-2-(4-methylphenylthio)-butyric acid 4-[2-(4-methylphenoxy)-ethoxy]-2-(4-methylphenyl-sulphonyl)-butyric acid 4-[2-(4-chlorophenoxy)-ethoxy]-2-(4-methylphenoxy)-butyric acid 4-[2-(4-chlorophenoxy)-ethoxy]-2-(4-methylphenylthio)-butyric acid 4-[2-(4-chlorophenoxy)-ethoxy]-2-(4-methylphenylsulphonyl)-butyric acid 4-[2-(4-chlorophenoxy)-ethoxy]-2-(2-phenylethylsulphonyl)-butyric acid 4-[2-(4-chlorophenoxy)-ethoxy]-2-(4-chlorocinnamylsulphonyl)-butyric acid 4-[2-(4-chlorophenoxy)-ethylthio]-2-(4-methylphenoxy)-butyric acid 4-[2-(4-methylphenoxy)-ethylthio]-2-(4-methylphenylsulphonyl)-butyric acid 4-[2-(4-chlorophenoxy)-ethylthio]-2-(4-methylphenoxy)-butyric acid 4-[2-(4-chlorophenoxy)-ethylthio]-2-(4-methylphenylsulphonyl)-butyric acid 4-[2-(4-chlorophenoxy)-ethylthio]-2-(4-methylphenoxy)-butyric acid 4-[2-(4-chlorophenoxy)-ethylthio]-2-(4-methylphenylsulphonyl)-butyric acid 4-[2-(phenylthio)-ethoxy]-2-(4-methylphenylsulphonyl)-butyric acid 4-[2-(phenylsulphinyl)-ethoxy]-2-(4-methylphenylsulphonyl)-butyric acid 4-[2-(phenylsulphonyl)-ethoxy]-2-(4-methylphenylsulphonyl)-butyric acid 4-[2-(phenylamino)-ethoxy]-2-(4-methylphenylsulphonyl)-butyric acid 8-(4-chlorophenoxy)-2-(4-methylphenoxy)-octanoic acid 8-(4-chlorophenoxy)-2-(4-methylphenylthio)-octanoic acid.

The following Examples are given for the purpose of illustrating the present invention:

EXAMPLE 1

8-Methoxy-2-(4-methylphenylsulphonyl)-octanoic acid

A solution of 1.38 g. (60 mmole) sodium in 500 ml. absolute enthanol is mixed, while stirring at boiling heat, with 14.5 g. (60 mmole) ethyl 4-methylphenylsulphonylacetate. For the completion of the salt formation, the reaction mixture is then stirred for 1 hour under reflux and subsequently a solution of 11.7 g. (60 mmole) 6-methoxyhexyl bromide is added dropwise thereto.

After further stirring for 5 hours at reflux temperature, the solvent is evaporated off and the residue is mixed with water. The organic parts are extracted with diethyl ether and the extracts are dried and evaporated. The residue is chromatographed with a mixture of heptane and butan-2-one (2:1 v/v) on silica gel to give 12.8 g. (64% of theory) ethyl 8-methoxy-2-(4-methylphenylsulphonyl)-octanoate in the form of a colourless oil.

2.5 g. (7 mmole) of this ester are stirred for 3 hours at 40° C. in a mixture of 15 ml. 1N aqueous potassium hydroxide solution and 50 ml. methanol. The methanol is then distilled off, the residue diluted with water and the neutral parts washed out with diethyl ether. The aqueous solution is subsequently clarified with charcoal, acidified and the separated product extracted with diethyl ether. The ether extracts are dried and evaporated and the oil remaining behind is stirred with a mixture of 0.58 g. (7 mmole) sodium hydrogen carbonate, 30 ml. ethanol and 30 ml. water for 1 hour, the clear solution obtained then being evaporated in a vacuum. The residue is triturated under heptane to give 1.8 g. (77% of theory) sodium [8-methoxy-2-(4-methylphenylsulphonyl)]-octanoate; m.p. 135°-139° C.

EXAMPLE 2

Ethyl 8-methylthio-2-(4-methylphenylsulphonyl)-octanoate

In a way analogous to that described in Example 1, from 21.8 g. (90 mmole) ethyl 4-methylphenylsulphonylacetate, 19.0 g. (90 mmole) 6-methylthiohexyl bromide and 2.07 g. (90 mmole) sodium there are obtained 22.5 g. (67% of theory) ethyl 8-methylthio-2-(4-methylphenylsulphonyl)-octanoate in the form of a colourless oil.

EXAMPLE 3

Ethyl 8-methylsulphonyl-2-(4-methylphenylsulphonyl)-octanoate.

A mixture of 4.0 g. (10.7 mmole) ethyl 8-methylthio-2-(4-methylphenylsulphonyl)-octanoate, 5.35 ml of a 4 molar solution of trifluoroperacetic acid in trifluoroacetic acid and 7.5 ml. trifluoroacetic acid is stirred for 4 hours at 0° c. The solvent is then distilled off in a vacuum and the residue taken up in diethyl ether. This solution is washed with aqueous sodium hydrogen carbonate, dried and evaporated. The residue is chromatographed with a mixture of toluene and dioxan (5:1 v/v) on silica gel to give 3.2 g. (60% of theory) ethyl 8-methylsylphonyl-2-(4-methylphenylsulphonyl-octanoate in the form of a colourless oil.

EXAMPLE 4

8-(4-Chlorophenyl)-2-(3-methylphenylsulphonyl)-octanoic acid.

A mixture of 87.5 g. (0.49 mole) sodium (3-methylphenyl)-sulphinate, 90.2 g. (0.54 mole) ethyl bromoacetate and 400 ml. ethanol is heated for 5 hours at reflux temperature. The solvent is then distilled off in a vacuum and the residue is taken up in water. The organic parts are extracted with diethyl ether and, after usual working up, distilled in a high vacuum to give 102.1 g. (86% of theory) ethyl 3-methylphenylsulphonylacetate; b.p. 157°-164° C./0.5 mbar.

To a solution of 36 mmole sodium methylate in 150 ml. absolute ethanol is added dropwise, while stirring at reflux temperature, a solution of 8.8 g. (36 mmole) ethyl 3-methylphenylsulphonylacetate in 50 ml. absolute ethanol and the mixture further stirred for 1 hour. 10.0 g. (36 mmole) 6-(4-chlorophenyl)-hexyl bromide are then added thereto and the reaction mixture again heated for 10 hours to reflux temperature. Subsequently, the reaction mixture is worked up as described in Example 1 and the residue is chromatographed with a mixture of heptane and butan-2-one (2:1 v/v) on silica gel to give 11.3 g. (72% of theory) ethyl 8-(4-chlorophenyl)-2-1-(3-methylphenylsulphonyl)-octanoate in the form of a colourless oil.

4.8 g. (11 mmole) of this ester are saponified in a mixture of 25 ml. 1N aqueous potassium hydroxide solution and 300 ml. methanol as described in Example 1 to give 4.3 g. (95% of theory) 8-(4-chlorophenyl)-2-(3- methylphenylsulphonyl)-octanoic acid in the form of a colourless oil.

EXAMPLE 5

4-[2-(4-Chlorophenyl)-ethoxy]-2-(4-methylphenylsulphonyl)-butanoic acid.

In a way analogous to that described in Example 1, from 13.2 g. (50 mmole) 2-[2-(4-chlorophenyl)-ethoxy]ethyl bromide (b.p. 170° C./20 mbar), 12.1 g. (50 mmole) ethyl 4-methylphenylsulphonylacetate and 1.15 g. (50 mmole) sodium there are obtained 19.0 g. (89% of theory) ethyl 4-[2-(4-chlorophenyl)-ethoxy]-2-(4-methylphenylsulphonyl-butanoate in the form of a colourless oil and therefrom 9.24 g. (75% of theory) sodium 4-[2-(4-chlorophenyl)-ethoxy]-2-(4-methylphenylsulphonyl)]butanoate; m.p. 70°-72° C. (amorphous).

By analogous methods, other compounds were also prepared, including:

EXAMPLE 6

5-(4-methylphenyl)-2-(4-methylphenyl sulphonyl)-4-pentynoic acid.

EXAMPLE 7

8-phenyl-2-(2-phenylethylsulphonyl)octanoic acid.

EXAMPLE 8

7-(4-chlorophenyl)-2-(2-methylphenylthio)-heptanoic acid.

EXAMPLE 9

7-(4-chlorophenyl)-2-(2-phenylethylsulphonyl)-heptanoic acid.

EXAMPLE 10

To show the blood glucose lowering action of the compounds of formula I the following experiments were performed:

In each case, groups of ten genetically diabetic OB/OB-mice were administered once per day the test substance for 5 days in a dosage of 100 ml/kg p. o. in tylose suspension. At the beginning of the experiment the average values of the glucose concentration in blood were identical within each group. A reference group of animals was given tylose p. o. only. During the whole period of the experiments the animals were given food and water ad libitum. Before the first administration of the substance and after the last administration, 0.01 ml blood were withdrawn from the tail veine. The determination of blood glucose was performed using the hexokinase method in haemolysate.

The therapeutic action of a test substance was characterized by its lowering effect on blood glucose (given in percent), taking into consideration the glycaemia of the reference group.

TABLE

| Compound of Example | blood glucose lowering effect in % |
|---|---|
| 1 (ester) | −19 |
| 1 (Na-salt) | −31 |
| 2 (ester) | −24 |
| 3 (ester) | −16 |
| 4 | −23 |
| 5 (Na-salt) | −29 |
| 6 | −5 |
| 7 | −25 |
| 8 | −10 |

TABLE-continued

| Compound of Example | blood glucose lowering effect in % |
|---|---|
| 9 | −38 |

It will be understood that the specification and examples are illustrative but not limitative of the present invention and that other embodiments within the spirit and scope of the invention will suggest themselves to those skilled in the art.

We claim:

1. Carboxylic acid derivatives of the formula

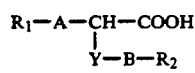

wherein $R_1$ is phenyl or phenoxy optionally substituted by halogen, $C_1$-$C_6$-alkyl, $C_1$-$C_6$-alkoxy, or trifluoromethyl;

$R_2$ is phenyl optionally substituted by halogen, $C_1$-$C_6$-alkyl, $C_1$-$C_6$-alkoxy, or trifluoromethyl, or, when B is alkylene, also a hydrogen atom;

A is a straight-chained or branched, saturated or unsaturated $C_3$-$C_{10}$ alkylene which is optionally interrupted by oxygen, sulphur, or —NH— attached to saturated carbon atoms, and has a chain length of at least 3 atoms, with the proviso that, where $R_1$ is phenyl, the chain length of saturated or ethylenically unsaturated alkylene is at least 4;

Y is an $S(O)_n$ group or an oxygen atom, n being 0, 1 or 2; and

B is a valency bond or a straight-chained or branched, saturated or unsaturated alkylene containing up to 5 carbon atoms;

and the physiologically acceptable salts, esters and amides thereof.

2. Carboxylic acid derivatives according to claim 1, wherein

A is a straight-chained or branched, saturated or unsaturated $C_3$-$C_{10}$ alkylene which has a chain length of at least 3 atoms.

3. Carboxylic acid derivatives according to claim 2, wherein $R_2$ is phenyl, 2-methylphenyl, 3-methylphenyl, 4-methylphenyl, 4-tert.-butylphenyl, 4-methoxyphenyl, 3-trifluoromethylphenyl or 4-dimethylaminophenyl.

4. Carboxylic acid derivatives according to claim 1, wherein

A is —$(CH_2)_m$— in which m is an integer from 3 to 10, or —$(CH_2)_p$—X—$(CH_2)_q$— in which p is an integer from 2 to 10, q is an integer from 1 to 6, the sum p and q being not greater than 10, and X is oxygen, sulphur or —NH—.

5. Carboxylic acid derivatives of the formula

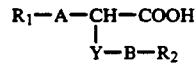

wherein $R_1$ is $C_6$-$C_{14}$ aryl optionally substituted by hydroxyl, halogen, $C_1$-$C_6$ alkyl, $C_1$-$C_6$ alkoxy, trifluoromethyl, cyano, nitro or amino optionally substituted by $C_1$-$C_6$ alkyl;

$R_2$ is $C_6$-$C_{14}$ aryl optionally substituted by hydroxyl, halogen, $C_1$-$C_6$ alkyl, $C_1$-$C_6$ alkoxy, trifluoromethyl, cyano, nitro or amino optionally substituted by $C_1$-$C_6$ alkyl; or, when B is alkylene also a hydrogen atom;

A is —CH$_2$—X—(CH$_2$)$_q$—, —CH=CHCH$_2$—, —C≡CCH$_2$—, C=C(CH$_2$)$_p$—, —CH=CHCH$_2$—X—(CH$_2$)$_g$— or —C≡CCH$_2$—X—(CH$_2$)$_q$—, in which p is an integer from 2 to 8, q is an integer from 1 to 6, and X is oxygen, sulphur or —NH—, with the proviso that, where $R_1$ is phenyl, A cannot be —CH=CHCH$_2$—;

Y is an S(O)$_n$ group or an oxygen atom, n being 0, 1 or 2; and

B is a valency bond or a straight-chained or branched, saturated or unsaturated alkylene containing 1 to 18 carbon atoms;

and the physiologically acceptable salts, esters and amides thereof.

6. Carboxylic acid derivatives according to claim 2, wherein

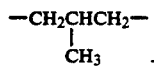

7. Carboxylic acid derivatives according to claim 5, wherein A is

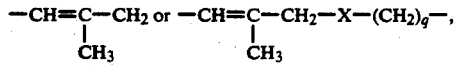

in which q is an integer from 1 to 6, and X is oxygen, sulphur or —NH—.

8. Carboxylic acid derivatives according to claims 1 or 5, wherein

B is —(CH$_2$)$_r$—, —CH$_2$—CH=CH—, —CH$_2$C≡C— or —CH=C—, in which r is an integer from 1 to 5.

9. Carboxylic acid derivatives of the formula

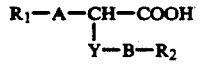

wherein $R_1$ is $C_1$-$C_8$ alkoxy, alkylthio, or alkylamino; $C_5$ or $C_6$ cycloalkyl or cycloalkoxy optionally substituted by methyl; phenyl, phenoxy, phenylthio, phenylsulphinyl, phenylsulphonyl, or phenylamino, optionally substituted by halogen, $C_1$-$C_4$ alkyl or trifluoromethyl;

$R_2$ is phenyl optionally substituted by halogen, $C_1$-$C_4$ alkyl, methoxy, trifluoromethyl, methylamino or dimethylamino, or, when B is an alkylene radical, also a hydrogen atom;

A is: $C_4$-$C_8$ alkylene with at least 4 carbon atoms in a straight chain; $C_4$-$C_6$ alkenylene or $C_3$-$C_6$ alkynylene with at least 3 carbon atoms in a straight chain;

alkylene-X-alkylene in which each alkylene has from 1 to 4 carbon atoms and X is oxygen, sulphur or —Nh—;

alkenylene-O-alkylene in which the alkenylene has from 3 to 5 carbon atoms, the oxygen atom is not attached to an unsaturated carbon atoms and the alkylene has from 1 to 3 carbon atoms;

alkynylene-O-alkylene in which the alkynylene has 3 or 4 carbon atoms, the oxygen atom is not attached to an unsaturated carbon atom and the alkylene has from 1 to 3 carbon atoms;

Y is S(O)$_n$ or oxygen in which n is 0, 1, or 2; and

B is a valency bond, $C_1$-$C_8$ alkyl or $C_2$-$C_8$ alkenyl;

and the physiologically acceptable salts, esters, and amides thereof.

10. Carboxylic acid derivatives of the formula

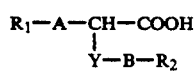

wherein p1 $R_1$ is methoxy; methylthio; methylamino; cyclopentyl; cyclohexyl; cyclohexyloxy; 1-methylcyclohexyloxy; phenyl optionally substituted by methyl, tert.-butyl, chlorine or trifluoromethyl; phenoxy optionally substituted by fluorine, chlorine, methyl or trifluoromethyl; phenylthio optionally substituted by chlorine; phenylsuphinyl optionally substituted by chlorine; phenylsulphonyl optionally substituted by chlorine; or phenylamino optionally substituted by chlorine;

$R_2$ is phenyl optionally substituted by chlorine $C_1$-$C_4$ alkyl, methoxy, trifluoromethyl or dimethylamino, or, when B is alkylene, also a hydrogen atom;

A is —(CH$_2$)$_{m'}$— in which m' is an integer from 4 to 10; —(CH$_2$)$_{q'}$—O—(CH$_2$)$_{q'}$— in which q' is an integer from 1 to 3; —C≡CCH$_2$—; —C≡C(CH$_2$)$_3$—; —(CH$_2$)$_2$—S—(CH$_2$)$_2$—; —(CH$_2$)$_2$—NH—(CH$_2$)$_2$—;

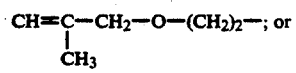

or C≡C—CH$_2$—O—(CH$_2$)$_2$—;

Y is oxygen, sulphur or —SO$_2$—; and

B is a valency bond, $C_1$-$C_8$ alkylene or —CH$_2$-CH=CH—;

and the physiologically acceptable salts, ester and amides thereof.

11. The compound according to claim 10, which is 8-methoxy-2-(4-methylphenylsulphonyl)octanoic acid.

12. The compound according to claim 10, which is ethyl 8-methylthio-2-(4-methylphenylsulphonyl)-octanoate.

13. The compound according to claim 10, which is 8-(4-chlorophenyl)-2-(3-methylphenylsulphonyl)-octanoic acid.

14. The compound according to claim 10, which is 4-[2-(4-chlorophenyl)-ethoxy]-2-(4-methylphenylsuphonyl)-butanoic acid.

15. The compound according to claim 10, which is 5-(4-methylphenyl)-2-(4-methylphenylsulphonyl)-4-pentynoicacid.

16. The compound according to claim 10, which is 8-phenyl-2-(2-phenylethylsulphonyl)-octanoic acid.

17. The compound according to claim 10, which is 7-(4-chlorophenyl)-2-(2-phenylethylsulphonyl)-heptanoic acid.

18. A pharmaceutical composition for the treatment of diabetic and fat-metabolic diseases which comprises an effective amount of a compound according to claims 1, 5, 9 or 10 and pharmaceutically acceptable carriers and adjuvant materials.

19. A composition according to claim 18, in which the compound is
8-methoxy-2-(4-methylphenylsulphonyl)-octanoic acid;
ethyl 8-methylthio-2-(4-methylphenylsulphonyl)-octanoate;
8-(4-chlorophenyl)-2-(3-methylphenylsulphonyl)-octanoic acid;
4-[2-(4-chlorophenyl)-ethoxy]-2-(4-methylphenylsulphonyl)-butanoic acid;
5-(4-methylphenyl)-2-(4-methylphenylsulphonyl)-4-pentynoic acid;
8-phenyl-2-(2-phenylethylsulphonyl)-octanoic acid; or
7-(4-chlorophenyl)-2-(2-phenylethylsulphonyl-heptanoic acid.

20. A method for the treatment of diabetic and fat-metabolic diseases which comprises administering an effective amount of a compound of the formula

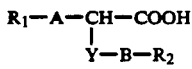

wherein
$R_1$ is: $C_1$-$C_8$ alkoxy, alkylthio, alkylsulphinyl, alkylsulphonyl, or alkylamino; $C_3$-$C_{10}$ cycloalkyl or cycloalkoxy optionally substituted by halogen or $C_1$-$C_6$ alkyl; or $C_6$-$C_{14}$ aryl, aryloxy, arylthio, arylsulphinyl, arylsulphonyl or arylamino optionally substituted by hydroxyl, halogen, $C_1$-$C_6$ alkyl, $C_1$-$C_6$ alkoxy, trifluoromethyl, cyano, nitro or amino optionally substituted by $C_1$-$C_6$ alkyl;
$R_2$ is an $C_6$-$C_{14}$ aryl optionally substituted by hydroxyl, halogen, $C_1$-$C_6$ alkyl, $C_1$-$C_6$ alkoxy, trifluoromethyl, cyano, nitro or amino optionally substituted by $C_1$-$C_6$ alkyl; or, when B is alkylene, also a hydrogen atom;
A is a straight-chained or branched, saturated or unsaturated $C_3$-$C_{10}$ alkylene which is optionally interrupted by oxygen, sulphur, or —NH— attached to saturated carbon atoms, and has a chain length of at least 3 atoms;
Y is an $S(O)_n$ group or an oxygen atom, n being 0, 1 or 2; and
B is a valency bond or a straight-chained or branched, saturated or unsaturated alkylene containing 1 to 18 carbon atoms;
and the physiologically acceptable salts, esters and amides thereof.

21. A method according to claim 20, wherein, in the compound,
$R_1$ is $C_1$-$C_8$ alkoxy, alkylthio, alkylsulphinyl, alkylsulphony1 or alkylamino; $C_3$-$C_{10}$ cycloalkyl or cycloakoxy; or phenyl, phenoxy, phenylthio, phenylsulphinyl, phenylsulphonyl or phenylamino optionally substituted by hydroxyl, halogen, $C_1$-$C_6$-alkyl, $C_1$-$C_6$-alkoxy, trifluoromethyl, cyano, nitro, amino, alkylamino or dialkylamino;
$R_2$ is phenyl, 2-methylphenyl, 3-methylphenyl, 4-methylphenyl, 4-tert.-butylphenyl, 4-methoxy, 3-trifluoromethylphenyl or 4-dimethylaminophenyl;
A is a straight-chained or branched, saturated or unsaturated $C_3$-$C_{10}$ alkylene which has a chain length of at least 3 atoms;
Y is oxygen, sulphur or —$SO_2$—; and
B is a valency bond or a straight-chained or branched, saturated or unsaturated alkylene containing 1 to 18 carbon atoms.

22. A method according to claim 21 in which the compound is
8-methoxy-2-(4-methylphenylsulphonyl)-octanoic acid;
ethyl 8-methylthio-2-(4-methylphenylsulphonyl)-octanoate;
8-(4-chlorophenyl)-2-(3-methylphenylsulphonyl)-octanoic acid;
4-[2-(4-chlorophenyl)-ethoxy]-2-(4-methylphenylsulphonyl-butanoic acid;
5-(4-methylphenyl)-2-(4-methylphenylsulpho)-4-pentynoic acid;
8-phenyl-2-(2-phenylethylsulphonyl)-octanoic acid; or
7-(4-chlorophenyl)-2-(2-phenylethylsulphonyl)-heptanoic acid.

23. A method according to claim 20, wherein from about 0.1 to about 15 mg per Kg of body weight are administered daily.

24. A method according to claim 20, which comprises the treatment of diabetes or pre-diabetic conditions.

25. A method according to claim 20, which comprises the treatment of fat metabolism diseases.

* * * * *

UNITED STATES PATENT AND TRADEMARK OFFICE
CERTIFICATE OF CORRECTION

PATENT NO. : 5,145,611
DATED : September 8, 1992
INVENTOR(S) : Wolff, et al.

It is certified that error appears in the above-identified patent and that said Letters Patent is hereby corrected as shown below:

Col. 3, line 44: change "heteroatoma" to -- heteroatom --.

Col. 9, line 49: change "7-2-[2-(4-" to -- 7-phenyl-2-[2-(4- --.

Col. 10, line 45: change "7-(4-methoxyphenyl)-2-(4-t-butylphenylsulphonyl)-I" to -- 7-(4-methoxyphenyl)-2-(4-t-butylphenylsulphonyl)-heptanoic acid --.

Col. 12, line 10: change "-heptanoic acid" to -- hexanoic acid --.

Col. 12, line 11: change "6-phenoxy-2-(4-methylphenythio)-heptanoic acid" to -- 6-phenylthio-2-(4-methylphenylthio)-hexanoic acid --.

Col. 12, line 12: change "6-phenoxy-2-(4-methylphenoxy)-heptanoic acid" to -- 6-phenylthio-2-(4-methylphenoxy)-hexanoic acid --.

Col. 12, line 13: change "6-phenoxy-2-(4-methylphenyl-sulphonyl)-heptanoic" to -- 6-phenythio-2-(4-methylphenylsulphonyl)-hexanoic --.

Col. 12, line 15: change "6-phenoxy-2-(4-methylphenoxy)-heptanoic" to -- 6-phenysulphonyl-2-(4-methylphenoxy)-hexanoic --.

UNITED STATES PATENT AND TRADEMARK OFFICE
CERTIFICATE OF CORRECTION

PATENT NO. : 5,145,611
DATED : September 8, 1992
INVENTOR(S) : Wolff, et al.

It is certified that error appears in the above-identified patent and that said Letters Patent is hereby corrected as shown below:

| | |
|---|---|
| Col. 12, line 16: | change "6-phenoxy-2-(4-methylphenylsulphonyl)-heptanoic" to -- 6-phenylsulphonyl-2-(4-methylphenylsulphonyl)-hexanoic --. |
| Col. 12, line 18: | change "6-phenoxy-2-(4-methylphenylsulphonyl)-heptanoic" to -- 6-phenylamino-2-(4-methylphenylsulphonyl)-hexanoic --. |
| Col. 12, lines 21-41: | change "heptanoic" to -- hexanoic --. |
| Col. 12, line 24: | change "6-4-chlorophenyl)-" to -- 6-(4-chlorophenyl)- --. |
| Col. 12, lines 26, 28 and 30: | change "6-4-chlorophenoxy)-" to -- 6-(4-chlorophenoxy)- --. |
| Col. 12, line 32: | change "6-4-chlorophenothio)-" to -- 6-(4-chlorophenylthio)- --. |
| Col. 12, lines 36-37: | delete "6-4-chlorophenthio)-2-(4-methylphenoxy)-heptanoic acid". |
| Col. 12, after line 41: | insert -- 6-(4-chlorophenylamino)-2-(4-methylphenoxy)-hexanoic acid --. |
| Col. 17, line 10: | change "$H_2$-X-$(CH_2)$g" to -- $H_2$-X-$(CH_2)$q --. |

UNITED STATES PATENT AND TRADEMARK OFFICE
CERTIFICATE OF CORRECTION

PATENT NO.   :   5,145,611
DATED        :   September 8, 1992
INVENTOR(S)  :   Wolff, et al.

It is certified that error appears in the above-identified patent and that said Letters Patent is hereby corrected as shown below:

| | |
|---|---|
| Col. 17, line 25: | after "wherein" on the next line insert -- A is --. |
| Col. 17, line 42: | delete "-CH=C" and insert -- —CH=CH --. |
| Col. 17, lines 41-42: | change "-CH-$_2$C=C-" to -- -CH$_2$C=C- --. |
| Col. 17, line 68: | change "Nh" to -- NH --. |
| Col. 18, line 25: | change "pl R$_1$ is" to -- R$_1$ is --. |
| Col. 18, line 47: | delete "C=C-CH$_2$-O-(CH$_2$)$_2$-". |
| Col. 18, line 49: | delete "or". |
| Col. 20, line 13: | change "sulphony l" to -- sulphonyl --. |
| Col. 20, line 38: | change "(4-methylphenylsulph)" to -- (4-methylphenylsulphonyl) --. |

Signed and Sealed this

Twelfth Day of April, 1994

BRUCE LEHMAN

*Attest:*

*Attesting Officer*

Commissioner of Patents and Trademarks